(12) United States Patent
Hu

(10) Patent No.: US 6,458,101 B1
(45) Date of Patent: Oct. 1, 2002

(54) SAFETY SYRINGE WITH RETRACTABLE NEEDLE HOLDER

(75) Inventor: Chien-Kung Hu, Miao Li Hsien (TW)

(73) Assignees: Li-Hua Lu (TW); Hung-Yang Fan (TW); Chu-Chun Chiu (TW)

( * ) Notice: Subject to any disclaimer, the term of this patent is extended or adjusted under 35 U.S.C. 154(b) by 0 days.

(21) Appl. No.: 09/867,530

(22) Filed: May 31, 2001

(51) Int. Cl.[7] .............................................. A61M 5/00
(52) U.S. Cl. ....................... 604/110; 604/110; 604/228; 604/218; 604/187; 604/194-196
(58) Field of Search ..................... 604/181, 186–188, 604/192, 195, 196, 198, 240–242, 243, 210, 220, 228

(56) References Cited

U.S. PATENT DOCUMENTS

| | | | | |
|---|---|---|---|---|
| 4,846,808 A | * | 7/1989 | Haber et al. ................ | 604/195 |
| 5,693,023 A | * | 12/1997 | Adams ........................ | 604/195 |
| 5,876,382 A | * | 3/1999 | Erickson .................... | 604/198 |
| 6,409,702 B1 | * | 6/2002 | Hu ............................. | 604/110 |

\* cited by examiner

*Primary Examiner*—Gregory L. Huson
*Assistant Examiner*—Anuradha Ramana
(74) *Attorney, Agent, or Firm*—Browdy and Neimark, P.L.L.C.

(57) ABSTRACT

A hypodermic syringe comprises a barrel having at least one catching piece disposed at the end; an outer sleeve fitted rotatably with the barrel to turn to locate at the first position and the second position and provided at least one escape hole; a needle holder having a cylinder cooperating portion disposed slidably in the receiving hole of the barrel, a retaining circular groove disposed in the outer periphery of the needle holder for retaining the catching piece of the barrel; a plunger having a rod body capable of pulling back the needle holder. As the outer sleeve is turned to the first position, each catching piece of the barrel retains the retaining tooth of the barrel. The needle holder is unable to displace. As the outer sleeve is turned to the second position, the escape hole is corresponding to the catching piece of the barrel to eject outward. The needle holder is not confined so as to be pulled back by the plunger.

14 Claims, 13 Drawing Sheets

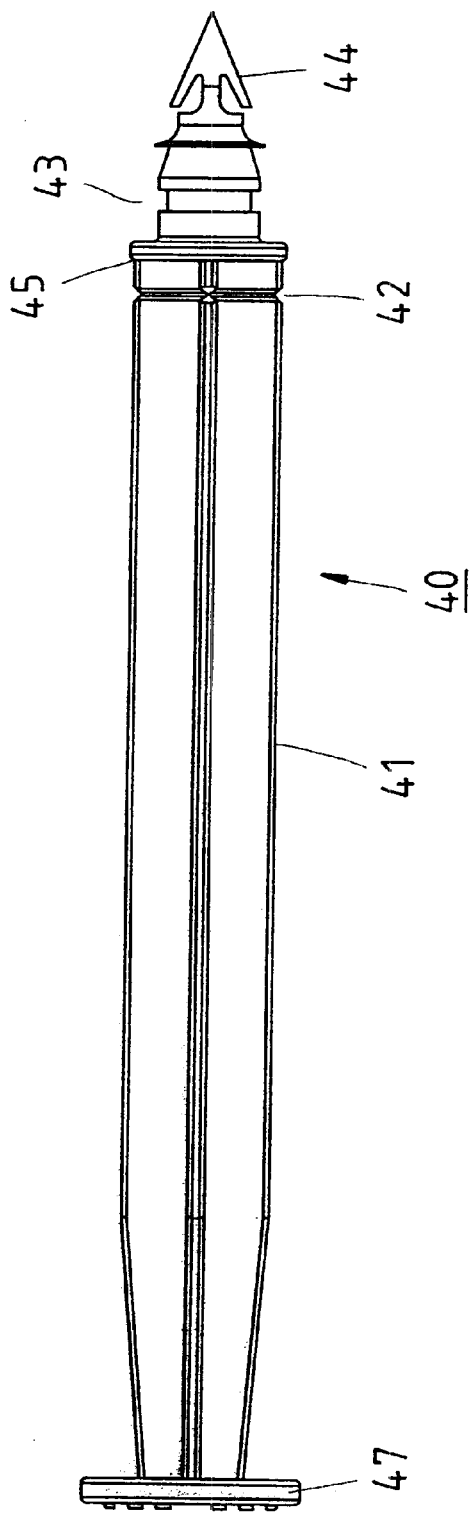
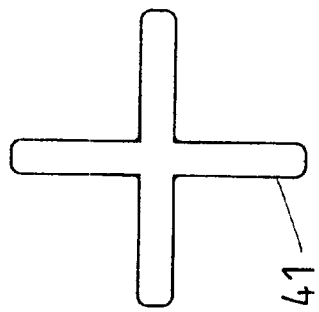
FIG. 13
FIG. 14

SAFETY SYRINGE WITH RETRACTABLE NEEDLE HOLDER

FIELD OF THE INVENTION

The present invention relates generally to a hypodermic syringe, and more particularly to a safety structure of the hypodermic syringe.

BACKGROUND OF THE INVENTION

The needle of a hypodermic syringe poses a safety hazard to the medical personnel. In light of high risk of infection of disease by the hypodermic needle, the conventional hypodermic syringes are generally provided with a needle which can be drawn into the barrel in the wake of hypodermic injection, thereby preventing the discarded syringe from becoming a potential safety hazard.

Such conventional hypodermic syringes as described above are defective in design in that they are complicated in construction, thereby resulting in high rejection rate. There are also certain similar hypodermic syringes which are rather simple in construction and can be made in quantity at a low cost; nevertheless they do not work with precision and are therefore not well received by the medical personnel at large.

SUMMARY OF THE INVENTION

It is the primary objective of the present invention to provide a hypodermic syringe with means to draw the hypodermic needle into the barrel of the syringe in the wake of injection.

It is another objective of the present invention to provide a hypodermic syringe with means to locate the needle holder thereof.

It is still another objective of the present invention to provide a hypodermic syringe which is simple in construction and works with precision.

The hypodermic syringe of the present invention comprises a barrel which is provided at a front end with at least one catching piece which is in turn provided in the inner edge with a retaining tooth. The barrel is provided with an outer ring and a locating projection. An outer sleeve has a ring body and an axial fitting hole for fitting over the barrel. A contraction edge is provided with an insertion hole. An inner protruded ring is disposed in the inner edge of the fitting hole. The ring body is provided at the front segment with at least one escape hole. A locating slot is provided with a first hole, a second hole, and a through hole. A protruded point slot channel extends from the outer end edge to the first hole. A needle holder has a barrel cooperating portion which is provided with outer circular groove to accommodate two O rings and is capable of sliding in the receiving hole of the barrel. A retaining shoulder is connected at one side of the barrel cooperating portion. A retaining circular groove is disposed in the outer periphery of the retaining shoulder. A fluid transporting hole is provided axially. A plunger has a rod body which is provided with a severing portion. A retaining hook is provided at the front end. The plunger is provided at the front end with a stopper.

The retaining tooth of the barrel catches the retaining circular groove of the needle holder by turning the outer sleeve in relation to the first position of the syringe, or turning the outer sleeve to the second position, thereby enabling the escape hole to be corresponding to the catching piece of the barrel, so as to eject outward. The needle holder is free to displace such that the needle is drawn back by the plunger.

BRIEF DESCRIPTION OF THE DRAWINGS

FIG. 13 shows a side view of the plunger of the preferred embodiment of the present invention.

FIG. 14 shows a cross-sectional view of the rod body of the plunger of the preferred embodiment of the present invention.

DETAILED DESCRIPTION OF THE INVENTION

Figure 1:
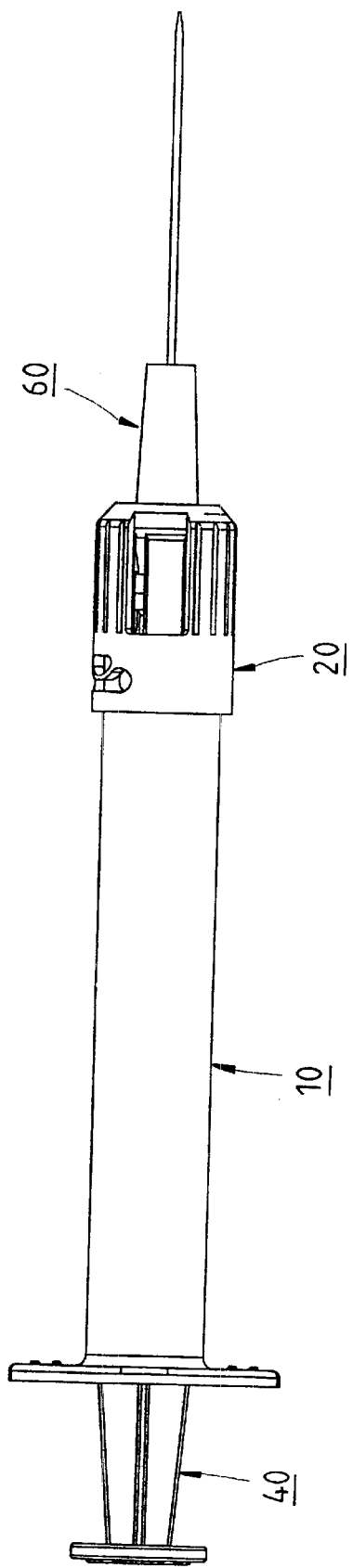
FIG. 1 shows an external plan view of a preferred embodiment of the present invention in combination.
Figure 2:
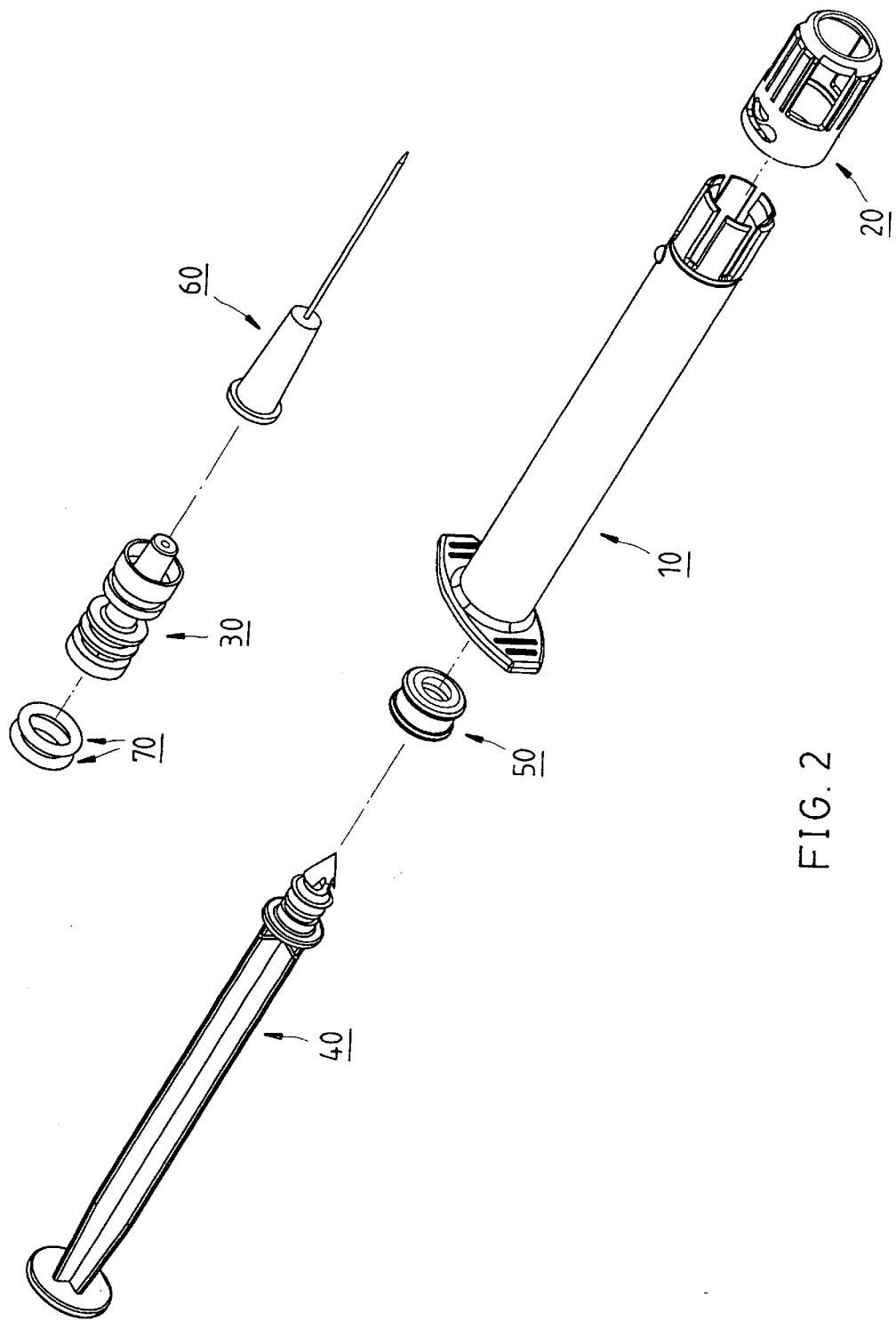
FIG. 2 shows an exploded view of the preferred embodiment of the present invention.
Figure 3:
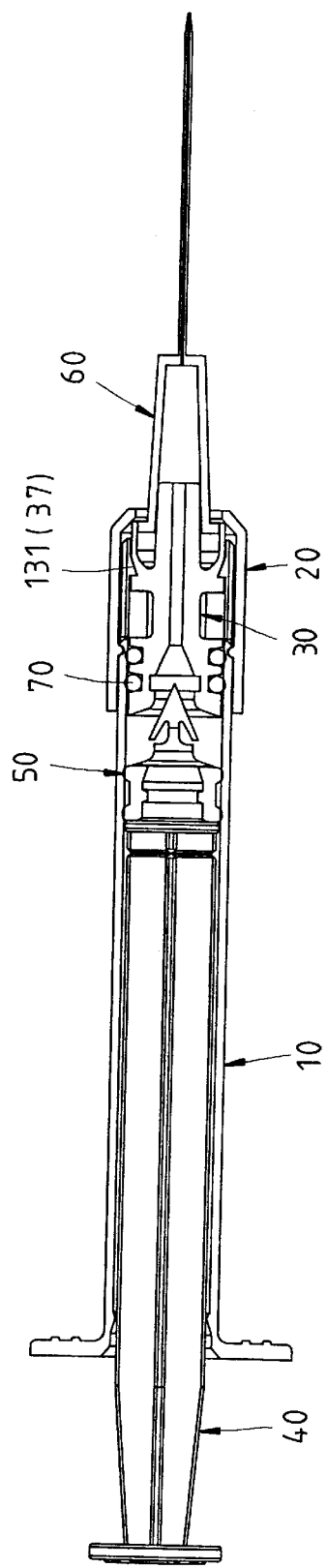
FIG. 3 is a side sectional view of the preferred embodiment of the present invention to show the non-retaining state before injection.

As shown in FIGS. 1–3, a hypodermic syringe embodied in the present invention has a hypodermic needle 60 and comprises the following component parts.

Figure 6:
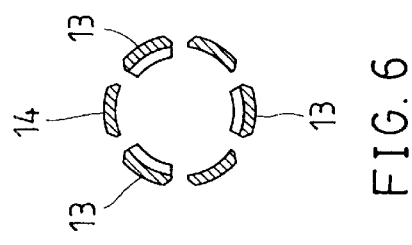
FIG. 6 shows a sectional view taken along a line 6—6 as shown in FIG. 4.
Figure 5:
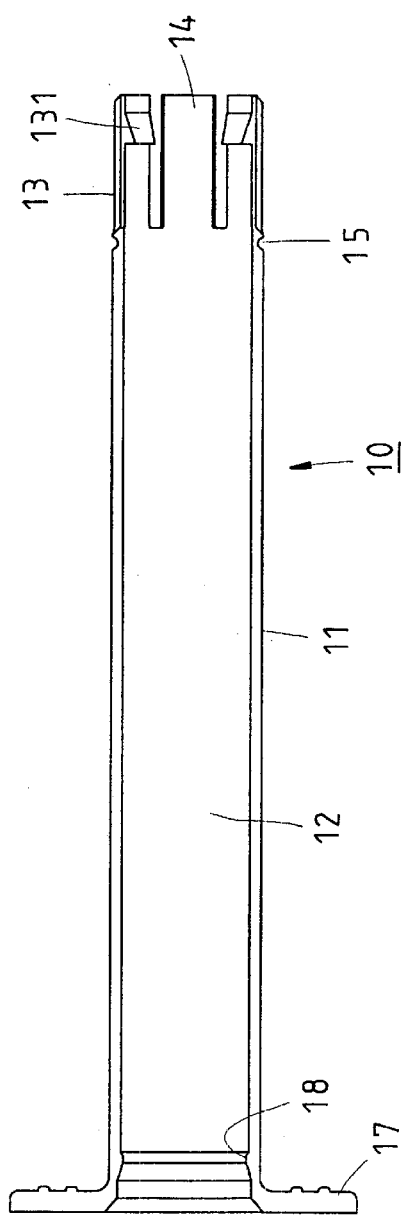
FIG. 5 shows a side sectional view of the barrel of the preferred embodiment of the present invention.
Figure 4:
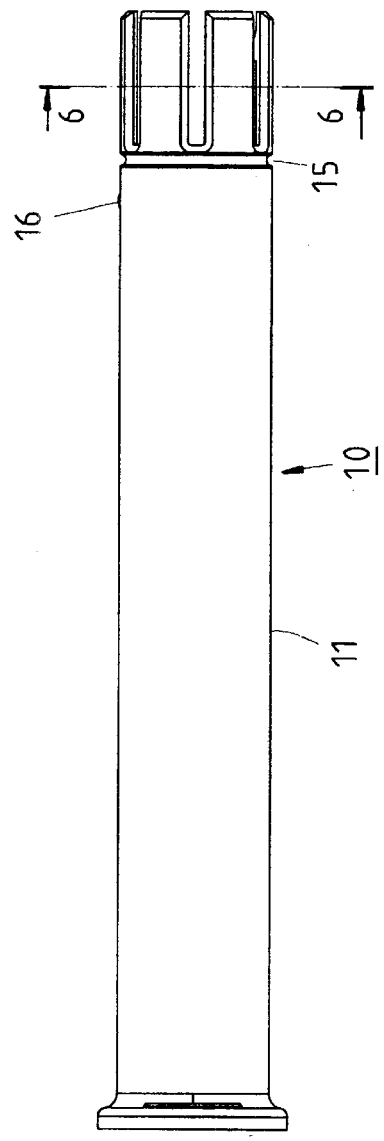
FIG. 4 shows a side view of the barrel of the preferred embodiment of the present invention.
Figure 7:
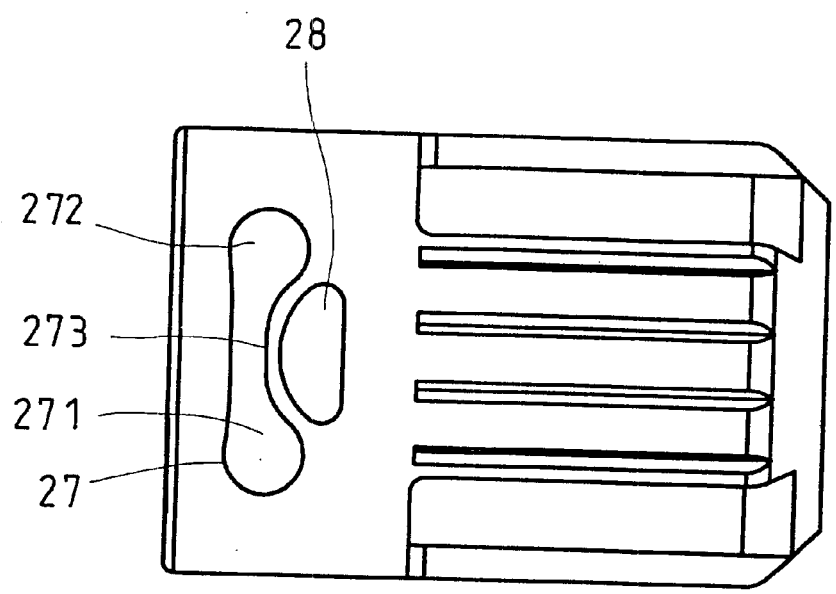
FIG. 7 shows a top view of the outer sleeve of the preferred embodiment of the present invention.
Figure 8:
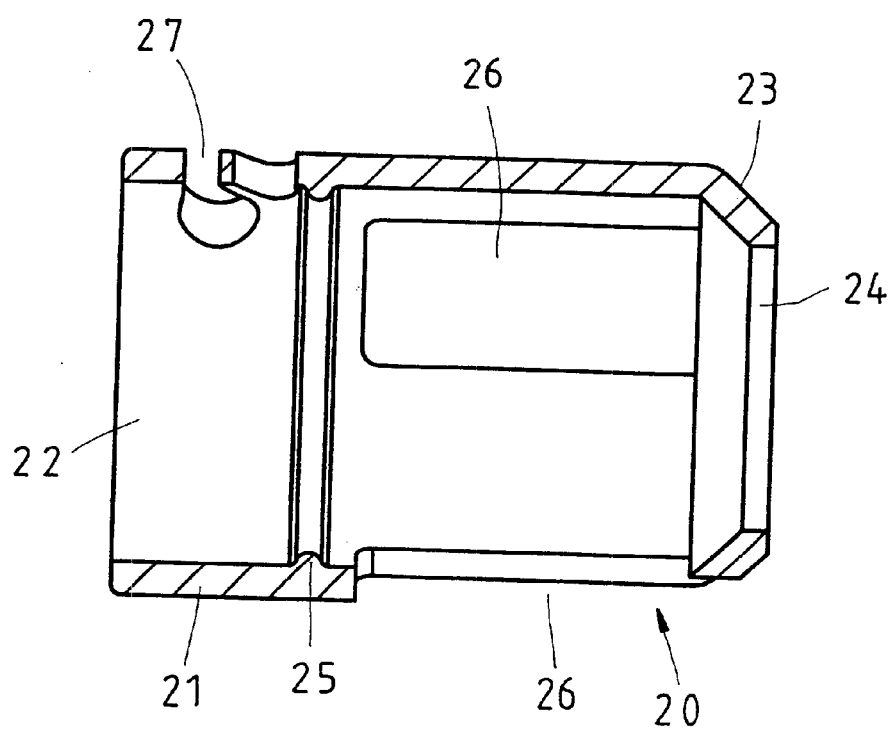
FIG. 8 shows a side sectional view of the outer sleeve of the preferred embodiment of the present invention.
Figure 9:
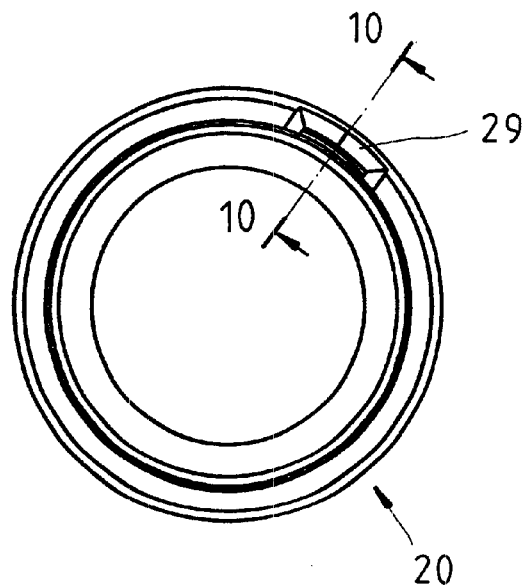
FIG. 9 shows an end view of the outer sleeve of the preferred embodiment of the present invention.
Figure 10:
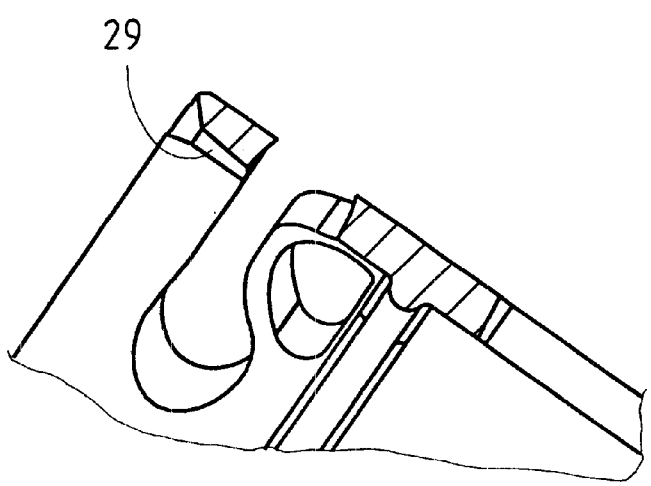
FIG. 10 shows an enlarged sectional view taken along a line 10—10 as shown in FIG. 9.

A barrel 10 has a cylinder body 11 which is provided with a receiving hole 12, three catching pieces 13 which are equidistantly arranged in the circumference of the front end of the cylinder body 11 and are provided in the inner edge with a retaining tooth 131, three partition pieces 14 which are disposed between the catching pieces 13, an outer circular groove 15 formed in the predetermined position of the outer periphery, a locating projected point 16 disposed on the outer periphery of the cylinder body 11, a hand holding lug 17 disposed in the outer side of other end of the cylinder body 11, a plunger stop edge 18 disposed in proximity of the opening of the receiving hole 12, as shown in FIGS. 4–6.

As shown in FIGS. 7–10, an outer sleeve 20 has an annular body 21 which is provided axially with a fitting hole 22 for fitting the cylinder body 11 of the barrel 10, a contraction edge 23 provided with an insertion hole 24, an inner protruded ring 25 disposed in the inner edge of the fitting hole 22, three escape holes 26 arranged equiangularly at the front segment of the annular body 21, a locating slot hole 27 provided with a first hole 271, a second hole 272, a protruded restriction portion 273 formed therebetween, an elastic hole 28 disposed in one side of the protruded restriction portion 273, and a protruded point slot channel 29 extending from the outer end edge to the first hole 271.

Figure 11:
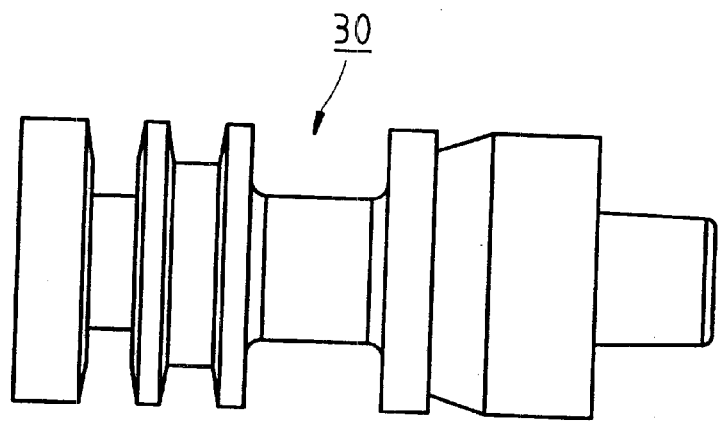
FIG. 11 shows a top view of the needle holder of the preferred embodiment of the present invention.
Figure 12:
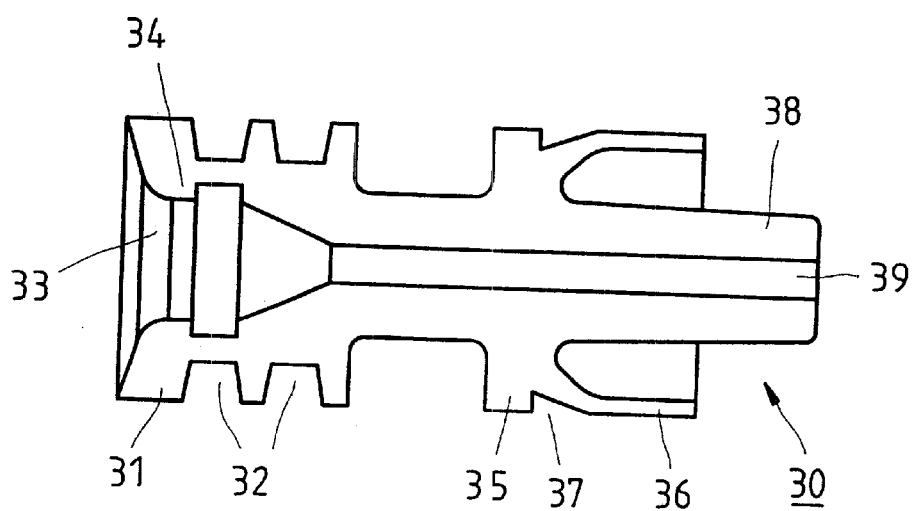
FIG. 12 shows a side sectional view of the needle holder of the preferred embodiment of the present invention.

As shown in FIGS. 11–12, a needle holder 30 has a barrel cooperating portion 31 and is provided with outer circular groove 32 for accommodating two O rings 70 and can be slidably plugged into the receiving hole 12 of the barrel 10, an insertion hole 33 forming inward a pull stop edge 34, a retaining shoulder 35 disposed in one side of the barrel cooperating portion 31, a protective sleeve 36 disposed at other end of the retaining shoulder 35, a retaining circular groove 37 disposed in the outer periphery of the retaining shoulder 35, a needle connecting tube 38 for connecting and fixing the needle 60, and a liquid transporting hole 39 connected with the insertion hole 33.

As shown in FIGS. 13–14, a plunger 40 has a rod body 41 of a cruciform cross section, a severing portion 42 disposed at a predetermined position, a neck 43 connected at the front end thereof, a hooked retainer 44 disposed at the farther front end, a stop disk 45 disposed between the severing portion 42 and the neck 43, and a push disk 47 disposed at the rear end thereof to facilitate the pushing of the plunger 40 by finger.

A stopper 50 has a circular body 51 which is provided in the center with a fitting hole 52 for fitting with the neck 43 of the plunger 40 such that its outer peripheral protruded ring is airtightly received in the receiving hole 12 of the barrel 10.

As shown in FIG. 3, the present invention is provided with the drug fluid to be injected hypodermically. The drug fluid is drawn in by pulling the plunger 40.

Figure 15:
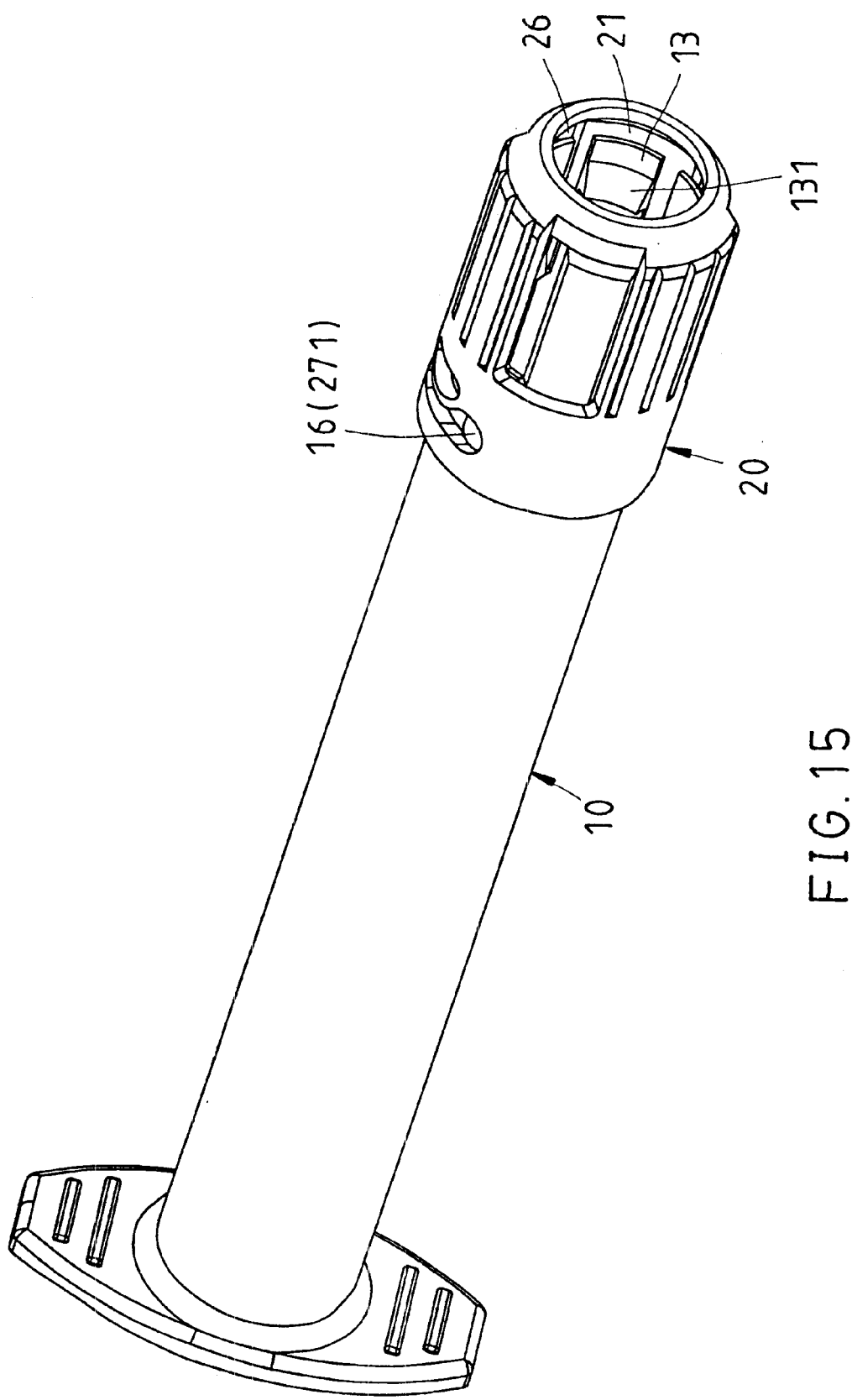
FIG. 15 is a perspective view of the syringe and the outer sleeve of the preferred embodiment of the present invention to show that they are so turned as to remain in the retaining state.

The needle holder 30 remains at this time in the fixation state. As shown in FIG. 15, the first hole 271 of the outer sleeve 20 is located at the locating projected point 16 (the first position) of the barrel 10. The retaining teeth 131 of the catching pieces 13 of the barrel 10 can not be expanded to deform, so as to keep each retaining tooth 131 in the retaining circular groove 37 of the needle holder 30, thereby preventing the needle holder 30 from displacing or swaying.

Figure 16:
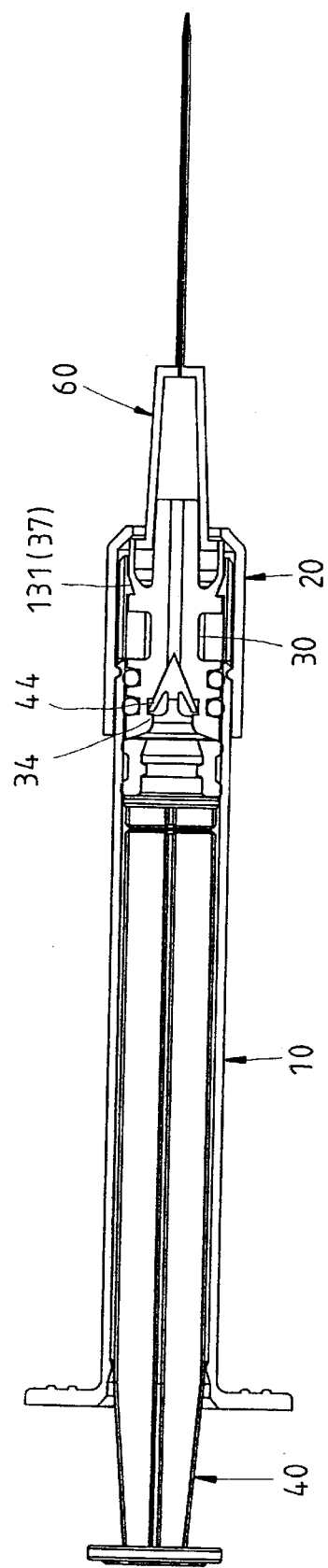
FIG. 16 is a sectional view of the preferred embodiment of the present invention to show that the plunger is in the retaining state in the wake of injection.

As shown in FIG. 16, the present invention has completed the hypodermic injection such that the hooked retainer 44 of the plunger 40 is located at the pull stop edge 34 of the needle holder 30. The plunger 40 and the needle holder 30 are in the linking state.

Figure 17:
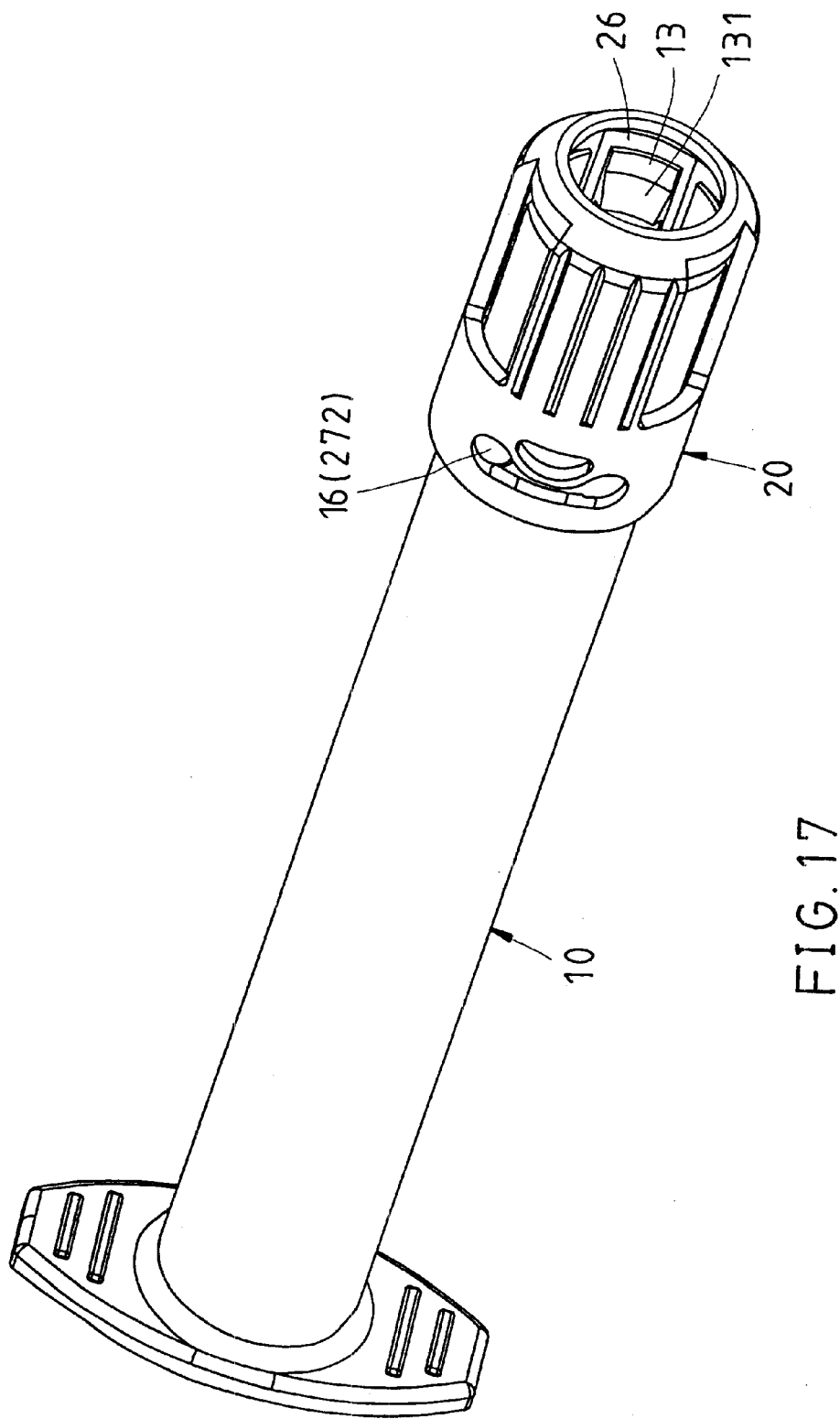
FIG. 17 is a perspective view of the syringe and the outer sleeve of the preferred embodiment of the present invention to show that they are so turned as to remain in the non-retaining state.

As shown in FIG. 17, the outer sleeve 20 is turned to enable the locating projected point 16 of the barrel 10 to pass the protruded restriction portion 273 of the outer sleeve 20 so as to locate at the second hole 272 (the second position).

Figure 18:
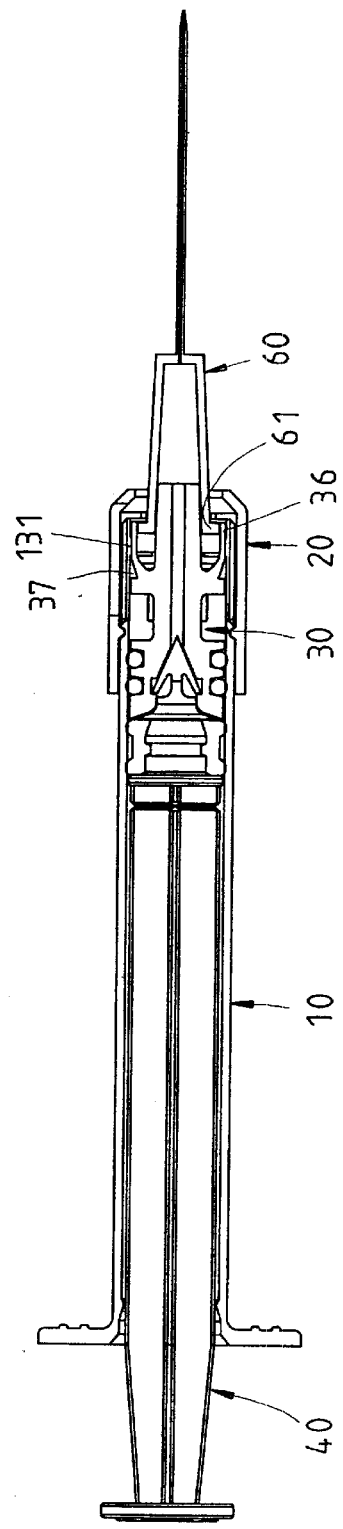
FIG. 18 is a sectional view of the preferred embodiment of the present invention to show that the needle holder is being drawn back by the plunger.
Figure 19:
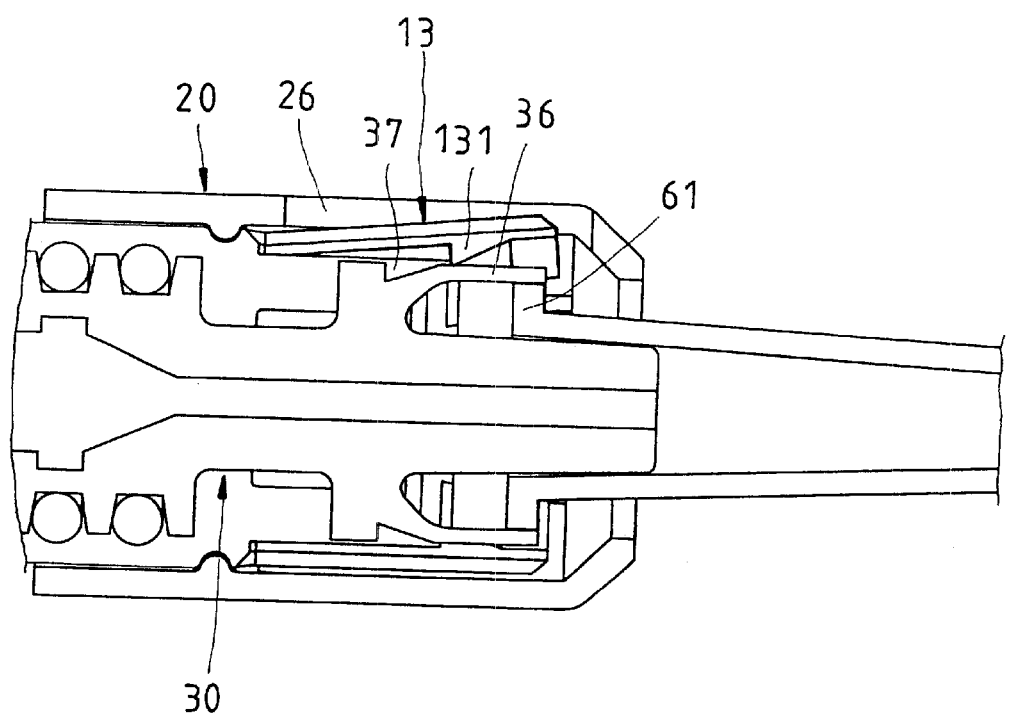
FIG. 19 is a partial enlarged view of FIG. 18.

As shown in FIGS. 18–19, each catching piece 13 of the barrel 10 is opposite in location in the escape hole 26 of the outer sleeve 20. As a result, when the plunger is pulled backward, the pull stop edge 34 of the needle holder 30 displaces to urge the catching piece 13 of the barrel 10 to expand toward the escape hole 26 of the outer sleeve 20, thereby causing the needle holder 30 to be drawn in.

At this time, the protective sleeve 36 of the needle holder 30 surrounds the sleeve head 61 of the needle 60, so as to prevent the needle 60 from being pressed against by the barrel 10 to detach.

Figure 20:
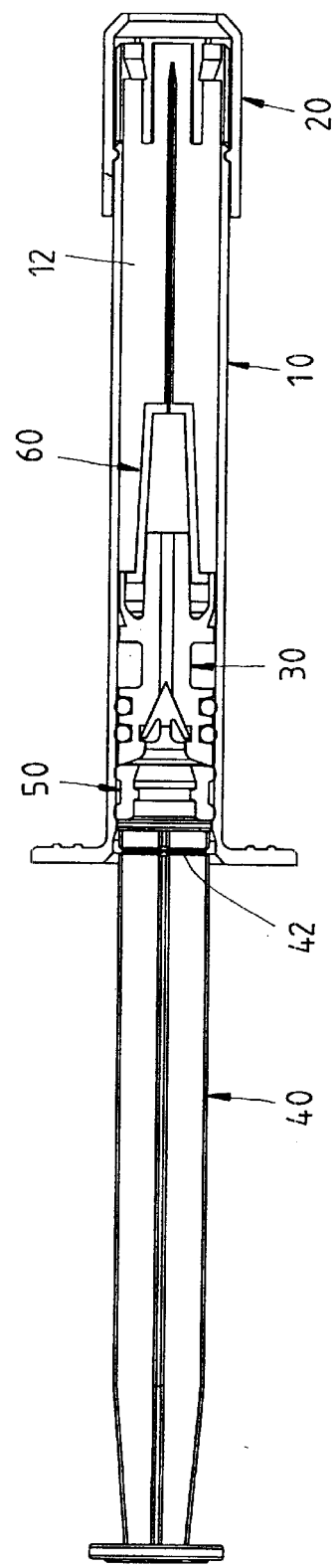
FIG. 20 is a sectional view of the preferred embodiment of the present invention to show that the needle holder has completely been drawn back by the plunger.

As shown in FIG. 20, the needle is already drawn in by the plunger such that the outer periphery of the stop disk 45 of the plunger 40 is stopped at the plunger stop edge 18 of the barrel 10. The plunger 40 is bent to break at the severing portion 42. The needle holder 30 and the needle 60 remain in the receiving hole 12 of the barrel 10.

The present invention has the following advantages over the prior art. In the first place, the needle and the needle holder of the syringe of the present invention are drawn in by the plunger at the same time, so as to enhance the safety of the present invention. The outer sleeve of the hypodermic syringe of the present invention can be turned to locate at various positions for locating the needle holder to enable the needle holder to displace. The design of the outer sleeve, the barrel and the needle holder of the present invention is relatively simple.

What is claimed is:

1. A hypodermic syringe having a hypodermic needle attached thereto, said hypodermic syringe comprising:

a barrel having a cylinder body which is provided with a receiving hole, and at least one catching piece disposed at the front end of said barrel and provided in the inner edge with a retaining tooth;

a rotatable outer sleeve having an annular body which is provided axially with a fitting hole for fitting with said cylinder body of said barrel, and at least one escape hole disposed at the front segment of said annular body, said outer sleeve being rotatable in relation to said barrel to locate at various positions;

a needle holder having a cylinder cooperating portion capable of sliding in said receiving hole of said barrel, a retaining circular groove disposed in the outer periphery thereof, and a liquid transporting hole extending axially;

a plunger having a rod body provided at a predetermined position with a severing portion, and a hooked retainer disposed at the front end;

a stopper fitted at the front end of said plunger and disposed in said receiving hole of said barrel;

said outer sleeve being rotatable in relation to a barrel first position so as to enable said retaining tooth of said barrel to catch said retaining circular groove of said needle holder, or rotating said outer sleeve to a second position to enable said escape hole thereof to be corresponding to said catching piece of said barrel to eject outward, thereby enabling said needle holder to displace to allow said plunger to pull back the needle.

2. The hypodermic syringe as defined in claim 1, wherein said escape hole of said outer sleeve is three in number, said three escape holes being arranged equiangularly in the front segment of said annular body.

3. The hypodermic syringe as defined in claim 2, wherein said catching piece of said barrel is three in number, said three catching pieces being disposed equidistantly in the circumference of the front end of said barrel.

4. The hypodermic syringe as defined in claim 3, wherein said outer sleeve further has three partition pieces which are respectively disposed between said catching pieces.

5. The hypodermic syringe as defined in claim 1, wherein said barrel further has in the outer periphery an outer circular groove, said outer sleeve having an inner protruded ring retained rotatably in said outer circular groove of said barrel.

6. The hypodermic syringe as defined in claim 1, wherein said barrel further has a locating projected point disposed in the outer periphery, said outer sleeve having a locating slot hole forming a first hole, a second hole, and a through hole connecting to locate at said locating projected point of said barrel.

7. The hypodermic syringe as defined in claim 6, wherein said outer sleeve further has a protruded point slot channel extending from outer end edge to said first hole for the passage of said locating projected point of said barrel.

8. The hypodermic syringe as defined in claim 6, wherein said outer sleeve further has a protruded restriction portion disposed in one end of said through hole.

9. The hypodermic syringe as defined in claim 1, wherein said needle holder is further provided with at least one outer circular groove to accommodate an O ring capable of being plugged into said receiving hole of said barrel.

10. The hypodermic syringe as defined in claim 1, wherein said needle holder is further provided with a contraction edge which is provided with an insertion hole to accommodate a sleeve head of the needle.

11. The hypodermic syringe as defined in claim 1, wherein said needle holder further has a pull stop edge, said plunger further having a hooked retainer disposed at the front end for retaining and pulling said pull stop edge of said needle holder.

12. The hypodermic syringe as defined in claim 1, wherein said plunger further has a neck which is disposed at the front end for a stopper to fit with.

13. The hypodermic syringe as defined in claim 1, wherein said needle holder further has a protective sleeve to accommodate said sleeve head of said needle so as to prevent the detachment of said needle at the time when said needle is being pulled back in.

14. The hypodermic syringe as defined in claim 1, wherein said needle holder further has a retaining shoulder which is disposed at one side of said cylinder cooperating portion to prevent displacement in relation to the front end direction of said barrel.

* * * * *